(12) United States Patent
Motta et al.

(10) Patent No.: US 8,729,308 B2
(45) Date of Patent: May 20, 2014

(54) PROCESS FOR THE PREPARATION OF TAPENTADOL AND INTERMEDIATES THEREOF

(75) Inventors: Giuseppe Motta, Rescaldina (IT); Domenico Vergani, Biassono (IT); Giorgio Bertolini, Sesto San Giovanni (IT)

(73) Assignee: Euticals S.p.A., Milan (IT)

( * ) Notice: Subject to any disclaimer, the term of this patent is extended or adjusted under 35 U.S.C. 154(b) by 0 days.

(21) Appl. No.: 13/512,989

(22) PCT Filed: Nov. 30, 2010

(86) PCT No.: PCT/IB2010/055499
§ 371 (c)(1),
(2), (4) Date: May 31, 2012

(87) PCT Pub. No.: WO2011/067714
PCT Pub. Date: Jun. 9, 2011

(65) Prior Publication Data
US 2012/0232306 A1    Sep. 13, 2012

(30) Foreign Application Priority Data
Dec. 1, 2009  (IT) .............................. MI2009A2110

(51) Int. Cl.
C07C 211/00    (2006.01)
C07C 221/00    (2006.01)
C07C 225/00    (2006.01)
C07C 223/00    (2006.01)

(52) U.S. Cl.
USPC ........................... 564/343; 564/336; 564/342

(58) Field of Classification Search
None
See application file for complete search history.

(56) References Cited

U.S. PATENT DOCUMENTS

| | | | |
|---|---|---|---|
| 3,824,271 | A | 7/1974 | Allen, Jr. et al. |
| 3,888,901 | A | 6/1975 | Allen et al. |
| 6,248,737 | B1 | 6/2001 | Buschmann et al. |
| 2006/0194988 | A1 | 8/2006 | Hell et al. |
| 2008/0269524 | A1 | 10/2008 | Buschmann et al. |

FOREIGN PATENT DOCUMENTS

| | | |
|---|---|---|
| EP | 0593475 | 1/1996 |
| WO | WO2006/012283 | 1/2008 |
| WO | WO2008/012047 | 1/2008 |

OTHER PUBLICATIONS

International Preliminary Report on Patentability for PCT/IB2010/055499 of Feb. 7, 2012.

International Search Report of PCT/IB2010/055499 of Mar. 31, 2011.

*Primary Examiner* — Clinton Brooks
(74) *Attorney, Agent, or Firm* — Hueschen and Sage

(57) ABSTRACT

The present invention refers to a new process for the synthesis of tapentadol comprising the quantitative resolution of the racemic mixture (V) to obtain the stereoisomer of (S)-3-(dimethylamino)-2-methyl-1-(3-nitrophenyl)-propan-1-one (VII) according to the Scheme 2 below

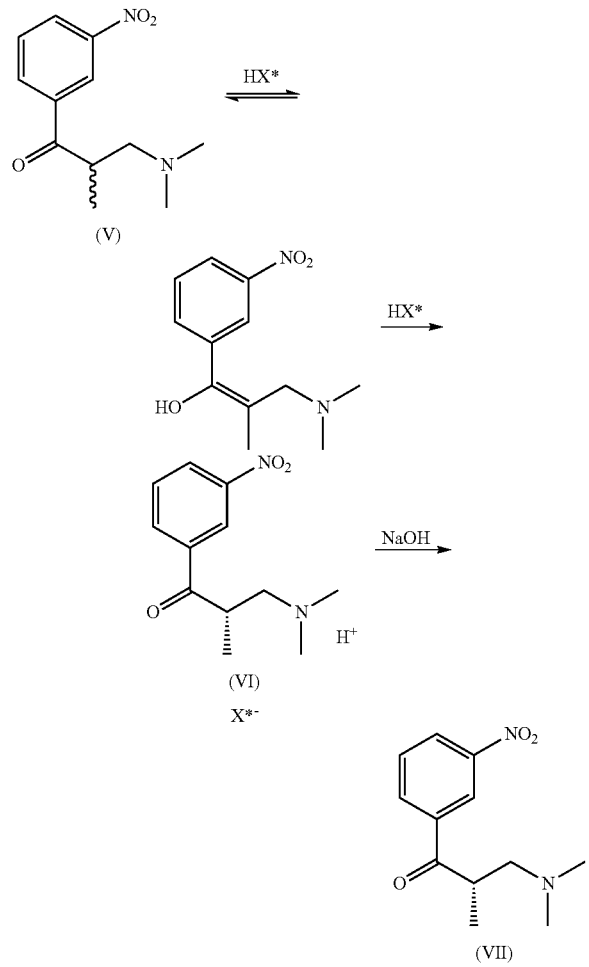

using the (2R,3R)—O,O'-dibenzoyltartaric chiral acid wherein said resolution is quantitative.

The present invention also refers to some intermediate compounds of the new synthesis process of tapentadol.

27 Claims, No Drawings

PROCESS FOR THE PREPARATION OF TAPENTADOL AND INTERMEDIATES THEREOF

TECHNICAL FIELD OF THE INVENTION

The present invention refers to a new process for the preparation of the 3-[(1R,2R)-3-(dimethylamino)-1-ethyl-2-methylpropyl]phenol, known by the name tapentadol, represented by the formula (I) indicated below

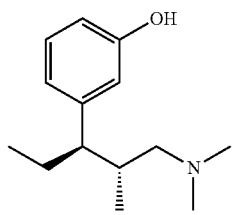
(I)

starting from the 1-(3-nitrophenyl)propan-1-one precursor having the formula (II) indicated below:

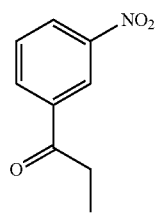
(II)

PRIOR ART

Tapentadol is a central action analgesic agonist of μ opioid receptors and noradrenaline reuptake inhibitor, used for treating acute pain from mild to severe. Derivatives with structure similar to tapentadol are described in literature.

U.S. Pat. No. 7,417,170 regards a process for synthesising with good yields 3-aryl-butyl-amine compounds by eliminating the tertiary alcoholic function from 4-amino-2-aryl-butan-2-ol compounds.

EP693475 describes the synthesis of 1-phenyl-3-dimethylamino-propane compounds having pharmacological activity.

U.S. Pat. No. 3,888,901 regards the synthesis of compounds of class of 3-alkyl-3-benzoyl-substituted)-propio nitrile, starting from phenyl alkyl ketones through Mannich reaction WO2008012047 indicates the synthesis of tapentadol, starting from 3-bromoanisole which, via organolithium, is converted into the 3-methoxy propiophenone. On this intermediate a Mannich reaction which leads to the racemic intermediate of formula (III) is carried out

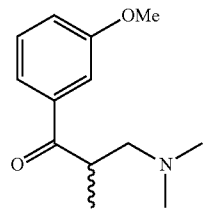
(III)

This intermediate (III) is subjected to enantiomeric separation through reaction with (2R,3R)—O,O'-dibenzoyltartaric chiral acid to obtain the preferred enantiomer of formula (IV):

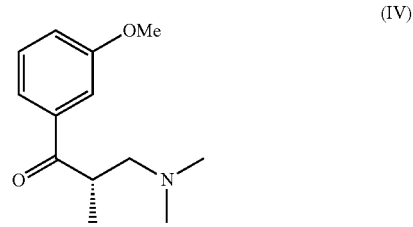
(IV)

However, this separation method is particularly disadvantageous in that it requires extremely long times and enables obtaining the dibenzoyltartaric salt of the desired isomer with low yields, i.e. about 75%.

The resolved enantiomer (IV) is thus alkylated through reaction with ethylmagnesium bromide and lastly the product of this reaction is hydrogenated and subsequently demethylated.

Thus, there still arises the need of a process for the production of tapentadol which enables obtaining this compound with high yields and high stereoselectivity.

DESCRIPTION OF THE INVENTION

The present invention regards a new synthesis of tapentadol starting from the 1-(3-nitrophenyl)propan-1-one compound of formula (II):

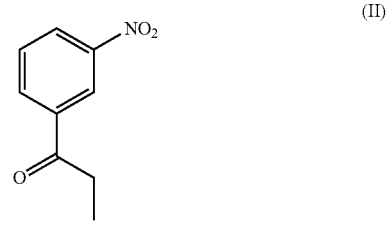
(II)

The compound (II), through Mannich reaction, is converted into the intermediate (V),

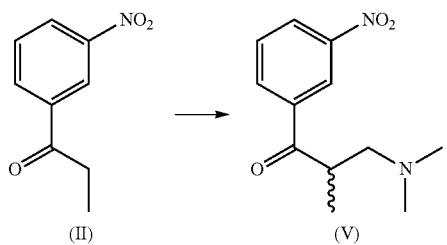

as a mixture of stereoisomers; which, in solution, interconverts according to the keto-enol equilibrium indicated in the scheme 1:

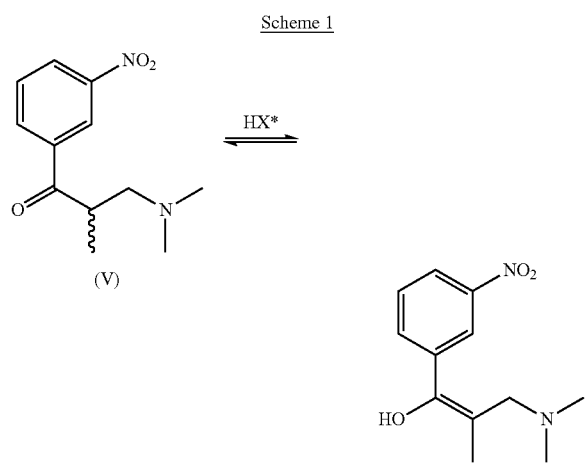

It was surprisingly found that the racemic mixture of the compound (V) can be resolved by quantitative conversion into the stereoisomer of interest (VII) using a chiral acid (HX*), such as (2R,3R)—O,O'-dibenzoyl tartaric acid, according to the scheme 2 below:

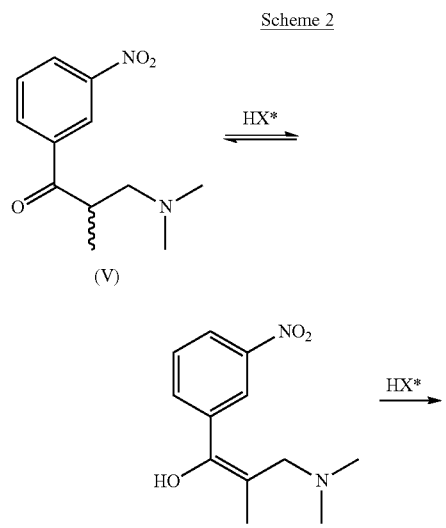

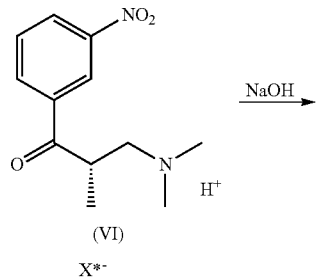

The desired isomer (VII) is obtained through a basic treatment of the precipitated salt (VI) after the reaction with the chiral acid.

The reaction of conversion into the preferred stereoisomer occurs quantitatively within a few hours with an indisputable advantage in terms of yield and production times.

In particular, the process according to the present invention allows obtaining the intermediate (VI) with markedly higher yields than those indicated in WO2008/012047A1, i.e. with yields of about 96%.

The resolved compound (VII) is converted into tapentadol through carbonyl alkylation by reaction with organometallic reagents, such as Grignard or diethylzinc reagents. There follows the reduction of the nitro group into an amino group and subsequent transformation thereof into a hydroxyl group, by forming the corresponding diazonium salt and hydrolysis thereof, where said steps are alternatively carried out according to scheme 3 or 4.

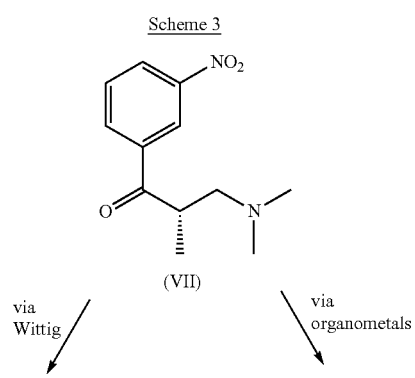

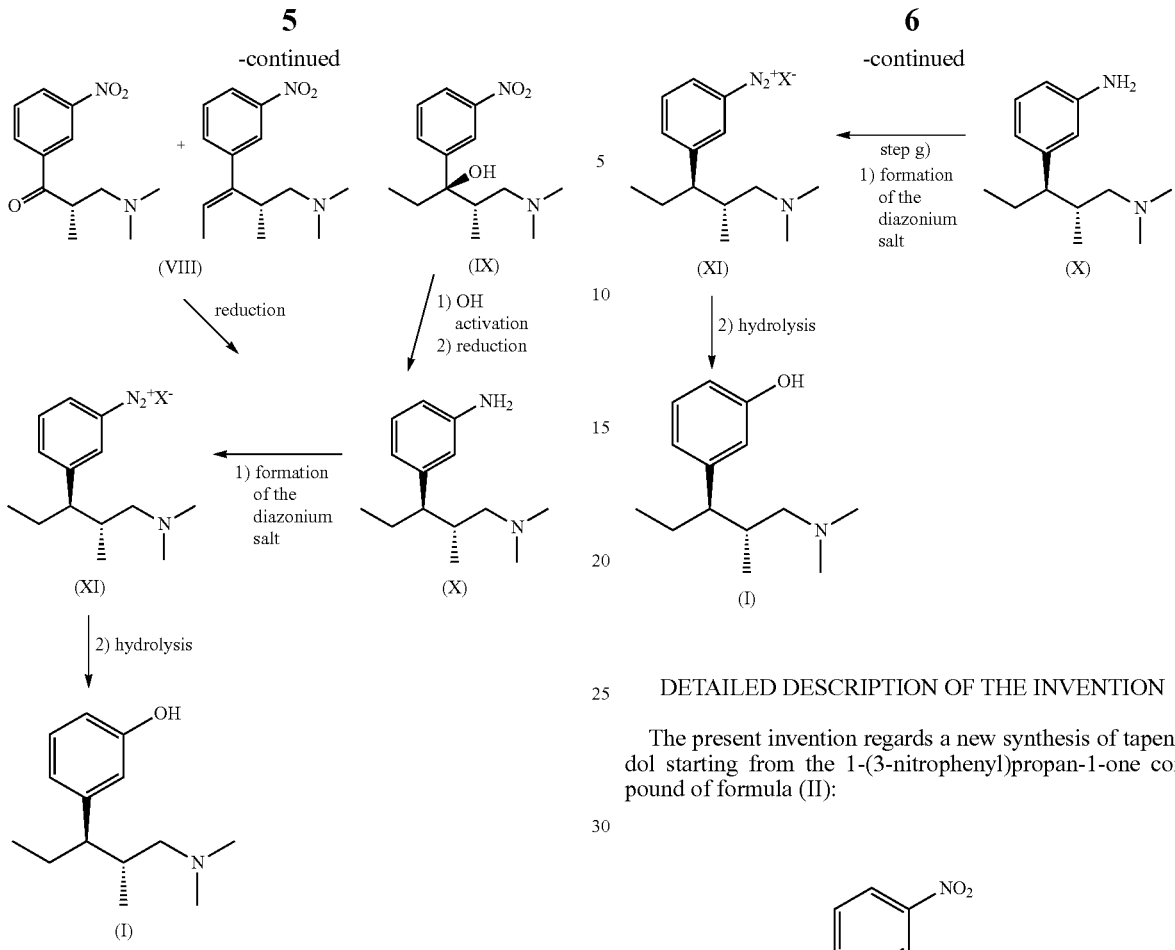

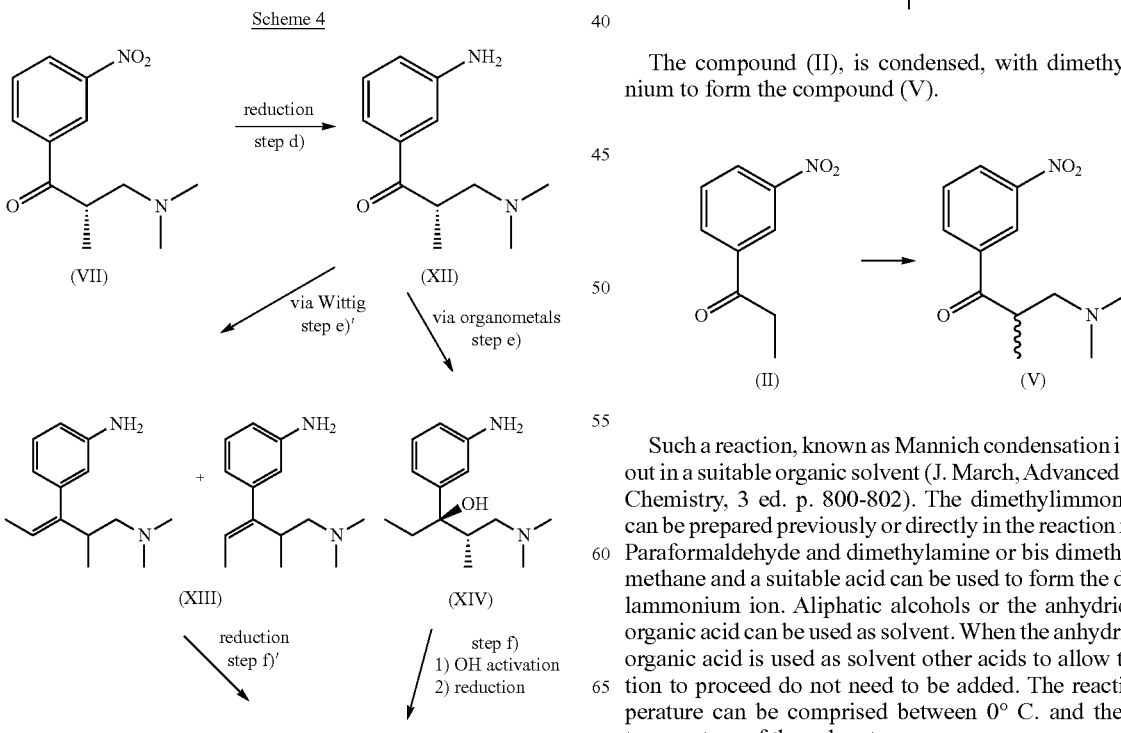

DETAILED DESCRIPTION OF THE INVENTION

The present invention regards a new synthesis of tapentadol starting from the 1-(3-nitrophenyl)propan-1-one compound of formula (II):

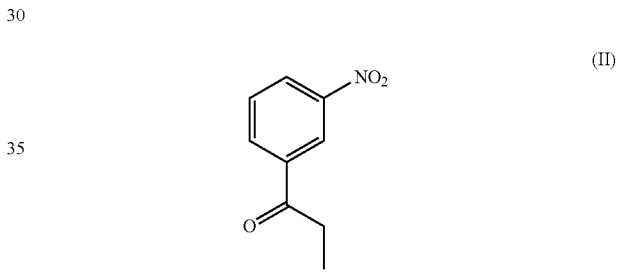

The compound (II), is condensed, with dimethylammonium to form the compound (V).

Such a reaction, known as Mannich condensation is carried out in a suitable organic solvent (J. March, Advanced Organic Chemistry, 3 ed. p. 800-802). The dimethylimmonium ion can be prepared previously or directly in the reaction mixture. Paraformaldehyde and dimethylamine or bis dimethylamino methane and a suitable acid can be used to form the dimethylammonium ion. Aliphatic alcohols or the anhydride of an organic acid can be used as solvent. When the anhydride of an organic acid is used as solvent other acids to allow the reaction to proceed do not need to be added. The reaction temperature can be comprised between 0° C. and the boiling temperature of the solvent.

In a preferred embodiment, the reaction conditions provide for the use of acetic anhydride, as solvent, and/or a temperature comprised between 50 and 80° C. Said reaction can be carried out as indicated in U.S. Pat. No. 3,824,271, herein incorporated by reference.

The product (V), obtained as mixture of stereoisomers, in solution interconverts according to the keton-enol equilibrium indicated in Scheme 1 described above. It was surprisingly found that this equilibrium can be moved quantitatively towards the enantiomer of interest by precipitating said enantiomer of interest as a chiral acid salt, as previously indicated in Scheme 2, by a suitable polar solvent or by a mixture of polar solvents. This enables obtaining the quantitative conversion of the mixture in the desired enantiomer. Water, aliphatic ketones, aliphatic alcohols, or any other polar solvent used separately or mixed with other polar solvents may be used for this separation as solvents. The preferred alcohols are methanol, ethanol, 1-propanol, 2-propanol and the preferred ketone is acetone. A methanol and acetone mixture is preferably used. (D)(−) mandelic acid, D(−) 2-chloro mandelic acid, D(−) tartaric acid, (2R,3R)—O,O'-dibenzoyl tartaric acid, preferably (2R,3R)—O,O'-dibenzoyl tartaric acid can be used as chiral acids. The salt of the resolved enantiomer is then suspended in a mixture of water and a suitable organic solvent. Adding an aqueous basic solution leads to releasing the stereoisomer (VII) from salt (VI), in form of free base. The compound (VII) is then extracted from the organic solvent from which it can be recovered by evaporation, while the salt of the chiral acid with the base remains in water and it can be recovered. Bases are selected from among a hydroxide of an alkaline or alkaline-earth metal, preferably sodium hydroxide or potassium hydroxide. Toluene, Cert-butylmethyl ether (MTBE), methyl isobutyl ketone (MiBK) are preferably used as organic solvent.

Said reaction sequence, which leads from the mixture (V) to the stereoisomer (VII), can be carried out as described in WO2008/012047A1, herein incorporated by reference. In WO2008/012047A1, said sequence differs from that of the present invention due to the presence of the methoxy group in position 3 of the benzene ring; in the present invention a nitro group is present in the benzene ring in position 3.

Thus, an object of the present invention is a new process for the synthesis of tapentadol of formula (I) comprising the step of quantitative resolution of the racemic mixture (V) to obtain the stereoisomer (VII), said step of resolution comprising the steps of a) reacting the racemic mixture of the compound (V) with a chiral acid in a polar solvent or mixture of polar solvents and subsequent precipitation of the chiral salt (VI);

b) treating the chiral salt (VI) with an aqueous basic solution to obtain the compound (VII);

c) subsequent extraction of the compound (VII) thus obtained with an organic solvent.

The compound (VII) is then treated so as to reduce the nitro group to an amino group (step d) to obtain the compound (XII), of formula:

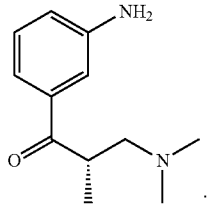
(XII)

This reduction can be carried out through the methods known in the art. Reduction with tin or catalytic hydrogenation are the preferred ones among these.

Reduction with tin is carried out by suspending tin shavings in a suitable organic solvent where the compound (VII) is also dissolved. Concentrated hydrochloric acid is dripped onto this suspension maintaining the temperature between 0° C. and the boiling temperature of the solvent. If the reaction was carried out in a water miscible solvent, this solvent is evaporated and it is substituted by a water immiscible solvent and then proceeding as follows.

The pH of the mixture is brought to values higher than 7, preferably between 10 and 13, using an inorganic base, preferably a hydroxide of an alkaline or alkaline-earth metal and even more preferably sodium hydroxide and potassium hydroxide, and an aqueous phase is separated. The organic phase can be used as it is in the subsequent step or concentrated up to the isolation of the product of hydrogenation as oil. The preferred solvents for this step are aliphatic alcohols for the reaction, preferably ethanol, and MTBE or toluene for the work-up. The reaction temperature is preferably between 35 and 50° C.

An alternative method for the reduction of the nitro group into an amino group, to obtain the compound (XII), can be catalytic hydrogenation. In this case the compound (VII) is dissolved in an organic solvent to which a catalyst is added. The mixture is then hydrogenated under pressure at a temperature comprised between −10 and 100° C. Upon completing hydrogenation, the catalyst is filtered. The hydrogenated product can be used in solution or isolated by evaporating the solvent.

Toluene, tetrahydrofuran (THF) and methyltetrahydrofuran (MeTHF) are the preferred solvents. Platinum or palladium on charcoal are the preferred catalysts. The reaction temperature is between 0 and 15° C.

The subsequent reaction sequence which leads from the compound (XII) to the compound (X) can be carried out as described in WO2008/012283A1, herein incorporated by reference. In WO2008/012283A1, said sequence differs from that of the present invention due to the presence of the methoxy group in position 3 of the benzene ring; in the present invention an amino group is present in the benzene ring in position 3. The presence of the methoxy group in position 3 of the benzene ring does not allow the formation of the intermediate compounds A and B, described in the present invention.

The compound (XII) obtained in the previous step is converted into the compound (XIV) in step e) by reaction with an organometallic compound. The organometallic compound can be purchased or prepared in situ by reacting the metal shavings with ethyl halide in a suitable organic solvent. The compound (XII) dissolved in an organic solvent which may not necessarily be the same used for the preparation of the organometallic reagent is dripped into the obtained organometal solution. The reaction temperature is maintained between 0° C. and the boiling temperature of the solvent. The metals used are preferably zinc and magnesium. The preferred ethyl halide is bromide and the temperature comprised between 10 and 30° C. 1 to 5 equivalents of organometallic reagent with respect to the compound (XII) are preferably used.

Upon completing the reaction the mixture is quenced by pouring it into an acid aqueous solution from which the compound (XIV) is extracted with an organic solvent. Ammonium hydrogen sulfate is preferably used for acidifying the aqueous phase. The compound (XIV) can be used as it is in the subsequent step or purified by the methods known in the art, preferably by crystallisation. A mixture of toluene and an aliphatic hydrocarbon is preferably used for crystallising the product (XIV).

The compound (XIV) is converted into the compound (X) in step f) by activating the hydroxyl of the compound (XIV) and subsequent reduction and hydrolysis. 1 to 5 equivalents of an anhydride or a halide of an organic acid with respect to the compound (XIV) are added to a solution of the compound (XIV), obtained directly from the previous step, or by dissolving the crystallised product in a suitable solvent. The anhydride or halide of the organic acid is preferably an anhydride or a halide of a substituted or unsubstituted aliphatic or aromatic organic acid, preferably a $C_1$-$C_5$ alkyl acid, optionally substituted with 1-3 halogen atoms; a benzoic acid, or a phenylacetic acid, optionally substituted with 1-3 halogen atoms, alkyl and/or carboxylic groups; $C_1$-$C_6$ dicarboxylic acids and $C_1$-$C_4$ aliphatic esters thereof.

Preferably said anhydride or halide of the organic acid are anhydrides or halides of acetic acid, phenylacetic acid, chloroacetic acid, trifluoroacetic acid, benzoic acid, chlorobenzoic acid, phthalic acid, succinic acid, oxalic acid or $C_1$-$C_4$ aliphatic monoesters of the oxalic acid or mixed anhydrides of the formic acid, even more preferably trifluoroacetic acid.

It is allowed to react up to complete esterification of the benzylic hydroxyl and conversion of aniline into amide, as indicated in Scheme 5, (compound (XV) when R=$CF_3$).

Alternatively this conversion can be carried out by adding a suitable organic acid and a dehydrating agent.

A catalyst, preferably palladium on charcoal is then added to the reaction mixture and hydrogenation is carried out at a pressure comprised between 1 and 100 bars and/or a temperature comprised between 0 and 100° C., as indicated in Scheme 5 (compound (XVI) when R=$CF_3$):

Scheme 5

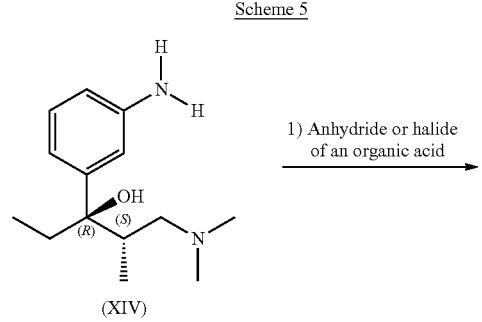

(XIV)
MW = 236.36
MF = C14H24N2O
(2S,3R) 3-(3-amino-phenyl)-1-dimethylamino-2-methyl-pentan-3-ol

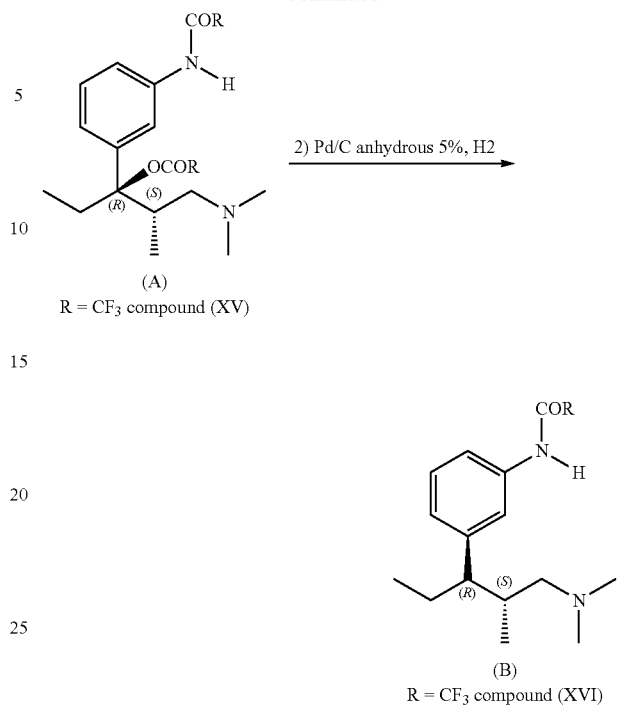

(A)
R = $CF_3$ compound (XV)

(B)
R = $CF_3$ compound (XVI)

In Scheme 5 R means:

$C_1$-$C_5$ alkyl, optionally substituted with 1-3 halogen atoms, or with a carboxylic group, possibly esterified with $C_1$-$C_4$ aliphatic alcohols, or, phenyl or benzyl, optionally substituted with 1-3 halogen atoms, with alkyl and/or carboxylic groups.

Preferably R is: H, $CH_3$, $CH_2Cl$, $CF_3$, $CH_2CH_2COOH$, $COOR^1$ where $R_1$ is H or $C_1$-$C_4$ alkyl, phenyl, chlorophenyl, o-carboxyphenyl radical.

Upon completing hydrogenation the catalyst is removed by filtration, the solution is concentrated and a basic aqueous solution for hydrolyzing the anilide is added. Upon completing hydrolysis, the product is extracted with a solvent immiscible in water and obtained as oil by concentration, as indicated in Scheme 6:

Scheme 6

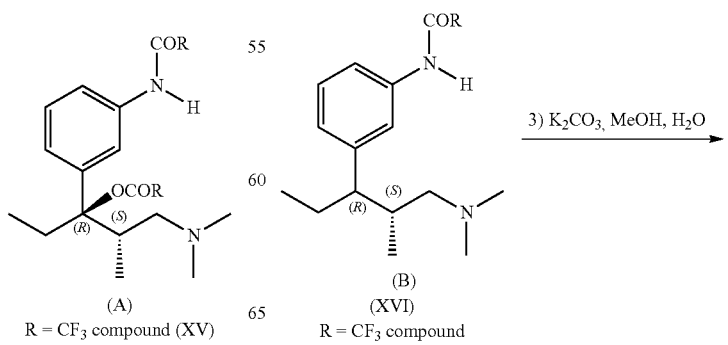

(A)
R = $CF_3$ compound (XV)

(B)
(XVI)
R = $CF_3$ compound

-continued

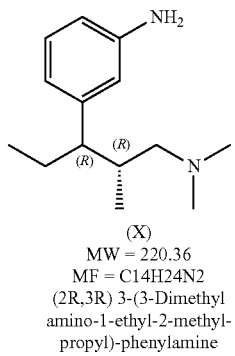

(X)
MW = 220.36
MF = C14H24N2
(2R,3R) 3-(3-Dimethyl
amino-1-ethyl-2-methyl-
propyl)-phenylamine Acid anhydrides or halides preferably used are substituted or unsubstituted aliphatic or aromatic organic acids. All condensing agents commonly used in organic chemistry can be used as condensing agents. Any inorganic base can be used as the base for the hydrolysis of the amide.

Alternatively, the compound (XII) can be converted into the compound (X) passing through the mixture of the isomer compounds (XIII) (step e)'), obtained through a Wittig reaction on the abovementioned compound (XII). According to this procedure, phosphorus ylides are used for converting the ketone compound of formula (XII) into the olefinic isomer compounds of formula (XIII). The compound (X) is then obtained from the mixture of isomers (XIII) by reduction (step f)').

The compound (X) is converted into tapentadol through hydrolysis of the corresponding diazonium salt (XI) (step g)). The product (X) is dissolved in an aqueous solution of a mineral acid to carry out this step. The preferred mineral acids for the reaction are: sulphuric acid, hydrochloric acid, phosphoric acid, methanesulfonic acid, trifluoroacetic acid, particularly sulphuric acid.

A saturated sodium nitrite solution is added to this solution maintained at a temperature between −15 and 50° C. Upon completing the reaction the obtained diazonium salt solution is dripped into a mineral acid solution maintained at a temperature between 50° C. and the boiling temperature of the acid. Upon completing the reaction, the mixture is cooled and brought to pH 10-11 with an inorganic base. Tapentadol is extracted using a suitable organic solvent and precipitated as a chlorohydrate by adding gaseous hydrochloric acid.

The preferred organic solvents for extracting tapentadol from the reaction mixture are aliphatic or aromatic hydrocarbons, in particular ethyl acetate, toluene, MiBK, MTBE and 3-pentanone are preferred.

A further aspect of the present invention is represented by the compounds of formula (A):

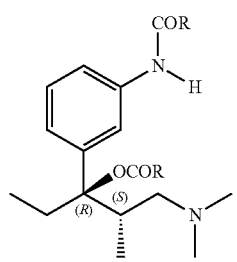

(A)

where R means: $C_1$-$C_5$ alkyl, optionally substituted with 1-3 halogen atoms, or with a carboxylic group, possibly esterified with $C_1$-$C_4$ aliphatic alcohols; or phenyl or benzyl, optionally substituted with 1-3 halogen atoms, with alkyl and/or carboxylic groups.

R preferably is H, $CH_3$, $CH_2Cl$, $CF_3$, $CH_2CH_2COOH$, $COOR^1$ where $R_1$ is H or $C_1$-$C_4$ alkyl, phenyl, chlorophenyl, o-carboxyphenyl radical, and even more preferably R is $CF_3$ (compound (XV), i.e. (2S,3R)-1-(dimethylamino)-2-methyl-3-(3-(2,2,2-trifluoroacetamido)-phenyl)pentan-3-yl 2,2,2-trifluoroacetate):

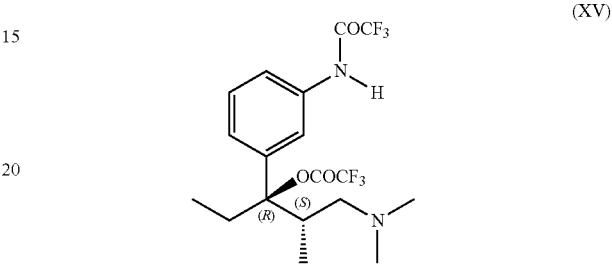

(XV)

These compounds are obtained as intermediates in the synthesis process of tapentadol object of the present invention.

A further aspect of the present invention is represented by the compounds of formula (B):

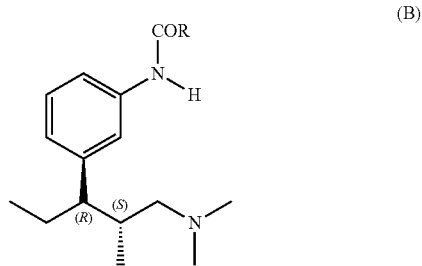

(B)

where R means: $C_1$-$C_5$ alkyl, optionally substituted with 1-3 halogen atoms, or with a carboxylic group, possibly esterified with $C_1$-$C_4$ aliphatic alcohols; or phenyl or benzyl, optionally substituted with 1-3 halogen atoms, with alkyl and/or carboxylic groups.

R preferably is H, $CH_3$, $CH_2Cl$, $CF_3$, $CH_2CH_2COOH$, $COOR^1$ where $R_1$ is H or $C_1$-$C_4$ alkyl, phenyl, chlorophenyl, o-carboxyphenyl radical, and even more preferably R is $CF_3$ (compound (XVI), i.e. N-(3-((2R,3S)-1-(dimethylamino)-2-methylpentan-3-yl)phenyl)-2,2,2-trifluoroacetamide):

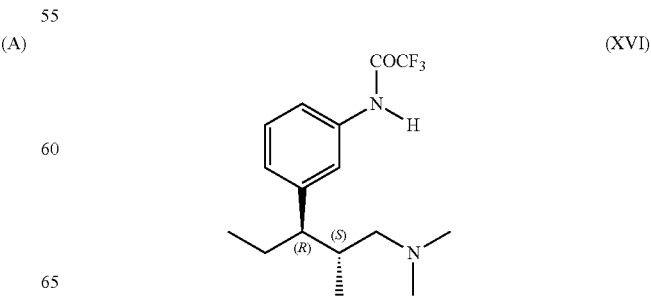

(XVI)

These compounds are obtained as intermediates in the synthesis process of tapentadol object of the present invention.

A further aspect of the present invention is represented by the compound of formula (VII), i.e. (S)-3-(dimethylamino)-2-methyl-1-(3-nitrophenyl)-propan-1-one:

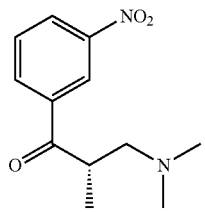

(VII)

as an intermediate in the synthesis process of tapentadol according to the present invention.

A further aspect of the present invention is represented by the compound of formula (XII), i.e. (S)-1-(3-aminophenyl)-3-(dimethylamino)-2-methylpropan-1-one:

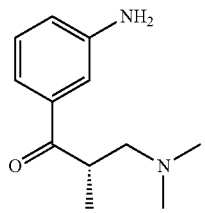

(XII)

as an intermediate in the synthesis process of tapentadol according to the present invention.

A further aspect of the present invention is represented by the compound of formula (XI), i.e. 3-((2R)-1-(dimethylamino)-2-methylpentan-3-yl)benzenediazonium:

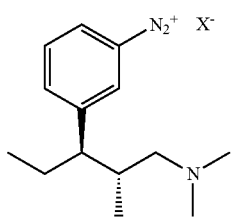

(XI)

as an intermediate in the synthesis process of tapentadol according to the present invention.

Uses as intermediates of the compounds of the general formula (A) or (B), where Rs are as defined above and in particular of the compounds of formula (XV), (XVI), (VII), (XII) and (XI) are also an object of the present invention.

The following examples shall be deemed solely by way of non-limiting example of the invention.

EXPERIMENTAL PART

Example 1

Preparation of 3-(dimethylamino)-2-methyl-1-(3-nitro-phenyl)-propan-1-one (V)

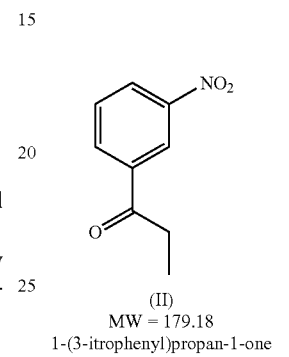

(II)
MW = 179.18
1-(3-itrophenyl)propan-1-one

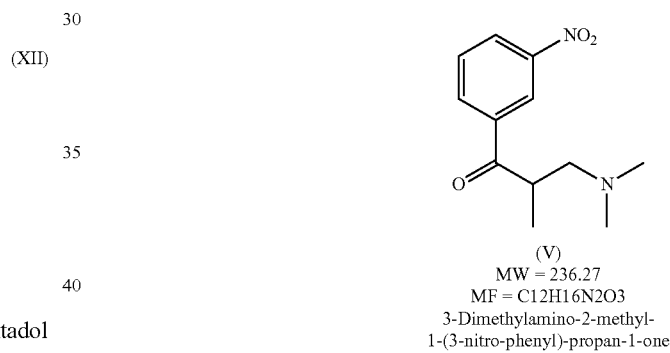

(V)
MW = 236.27
MF = C12H16N2O3
3-Dimethylamino-2-methyl-
1-(3-nitro-phenyl)-propan-1-one N,N-dimethylamine HCl (80.0 g, 0.982 mol), paraformaldehyde (45 g, 1.499 mol), water (30 g, 1.667 mol) and acetic anhydride (30 ml/32.4 g, 0.32 mol) are added into a 1 liter four-neck flask, provided with mechanical stirrer, thermometer and dropping funnel. The suspension is slowly heated up to 50° C. and stirred for 30 minutes. Then, acetic anhydride (200 ml/216 g, 2.12 mol) is dripped thereinto slowly and portionwise. The reaction mixture is stirred at 50-70° C. for at least 1 hour then 1-(3-nitrophenyl)propan-1-one (150 g, 0.837 mol) and acetic anhydride (200 ml/216 g, 2.12 mol) suspension is added. The reaction mixture is stirred at about 70° C. for 16 hours, then conversion is monitored using HPLC. When the conversion is >90% about 200 ml of solvent are distilled under vacuum and 600 ml of ethanol are added. The obtained suspension is cooled to 20-25° C. and allowed to stir for 3 hours. Then it is filtered and washed with 300 ml of acetone. About 210 g of almost colourless solid and with HPLC purity >99% are obtained. The wet product is suspended in water (600 ml), t-butyl-methylether (600 ml) and the pH is adjusted to 10-12 with 28% sodium hydroxide. The two phases are stirred for about 30 minutes then they are separated. The organic phase is concentrated to oily residue.

About 182 g of slightly yellowish oil (about 92% yield) with HPLC purity >99% are obtained.

Preparation of (S)-3-(dimethylamino)-2-methyl-1-(3-nitrophenyl)-propan-1-one (VII)

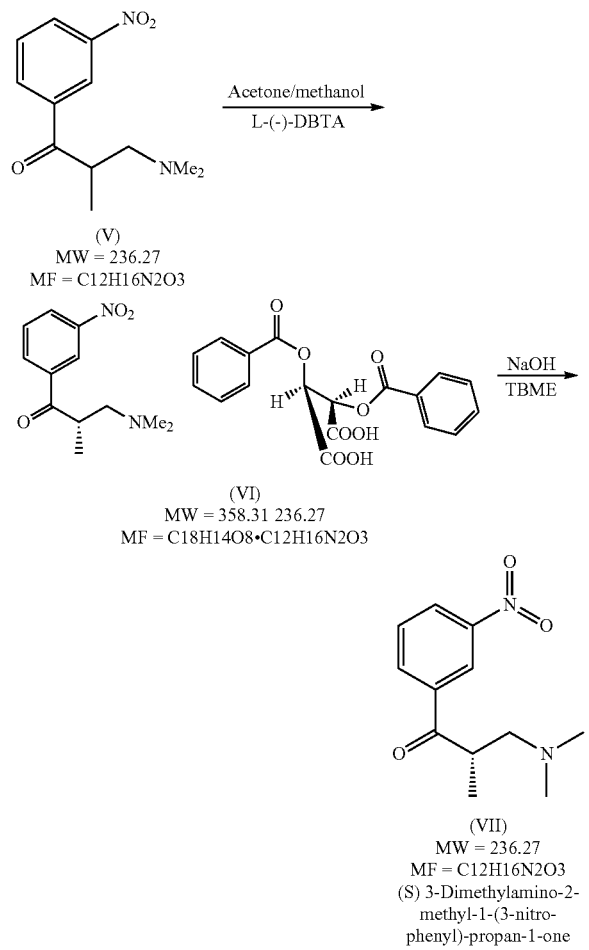

(2R,3R)—O',O'-dibenzoyl tartaric acid, $H_2O$ (159 g, 0.423 mol) in acetone (500 ml) are added into a 1 liter four-neck flask, provided with mechanical stirrer, thermometer and dropping funnel. The suspension is stirred at 35-40° C. up to complete dissolution, then a solution of 3-(dimethylamino)-2-methyl-1-(3-nitrophenyl)-propan-1-one (100 g, 0.423 mol) is dripped into methanol (83 ml). The suspension is stirred for 1-4 hours at 35-40° C. and for 24 hours at 20-25° C. then filtration is carried out and the solid is washed with acetone. The solid is suspended in 500 ml of acetone, heated at 50° C. for 2 hours and then stirred for other 2 hours at 25° C. Then the suspension is filtered and washed with acetone. About 320 g wet of (S)-3-(dimethylamino)-2-methyl-1-(3-nitrophenyl)-propan-1-one (2R,3R)—O-O'-dibenzoyltartrate are obtained as a colourless solid with ee≥98.5% which when dried give 242 g corresponding to a 96.2% yield calculated on the initial oil. The product is suspended in water (900 ml), t-butyl-methylether (900 ml) and the pH is adjusted to 10-12 with 28% sodium hydroxide. The two phases are separated and the organic phase is concentrated to oily residue. About 95 g of slightly yellowish oil (S)-3-(dimethylamino)-2-methyl-1-(3-nitrophenyl)-propan-1-one (about 95% yield) with HPLC purity ≥99% and ee ≥98.5% are obtained.

Preparation of the (S)-3-(dimethylamino)-2-methyl-1-(3-aminophenyl)-propan-1-one (XII)

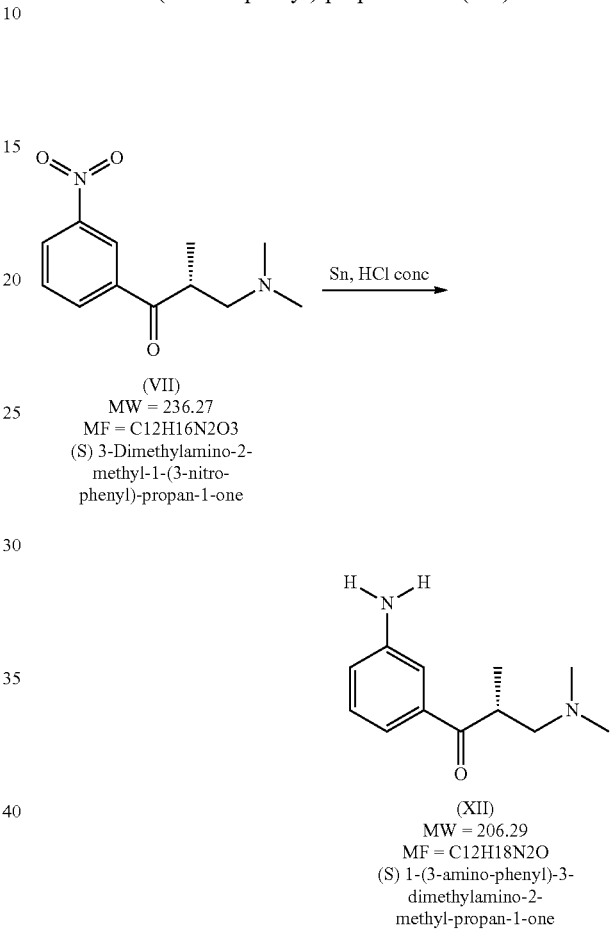

Granular tin (84.4 g, 0.711 moles), ethanol (210 ml), (S)-3-(dimethylamino)-2-methyl-1-(3-nitro-phenyl)-propan-1-one (105 g, 0.444 mol) are added into a 1 liter four-neck flask, provided with mechanical stirrer, thermometer and dropping funnel. The suspension is heated to 35° C. and 36% hydrochloric acid (210 ml) is added portionwise and maintaining the temperature between 35-50° C. The reaction is stirred at 35° C. for 3 hours then monitored using HPLC. 700 ml of ethanol 700 ml are added upon completing the reaction. The mixture is cooled at 0-4° C. for 16-24 hours. Then it is filtered and washed with acetone. About 150 g of yellowish solid with HPLC purity ≥99% are obtained. The wet product is suspended in water (200 ml), t-butyl-methylether (300 ml) and the pH is adjusted with 28% sodium hydroxide to ≥13.0. The two phases are stirred for about 30 minutes then they are separated. The organic phase is concentrated to an oily residue. About 62 g (about 69% yield) of reddish oil with HPLC purity ≥99% are obtained.

Alternative Method:

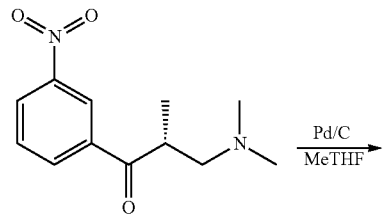

(VII)
MW = 236.27
MF = C12H16N2O3
(S) 3-Dimethylamino-2-methyl-1-(3-nitro-phenyl)-propan-1-one

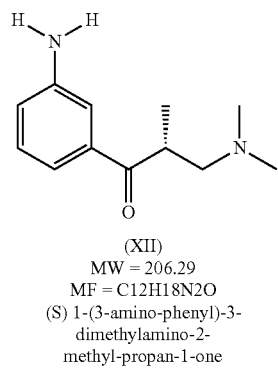

(XII)
MW = 206.29
MF = C12H18N2O
(S) 1-(3-amino-phenyl)-3-dimethylamino-2-methyl-propan-1-one (S)-3-(dimethylamino)-2-methyl-1-(3-nitro-phenyl)-propan-1-one (100 g, 0.423 mol), methyl-tetrahydrofuran (400 ml) and Pd/C 5%, anhydrous (4.0 g) are added into a 1 liter autoclave, at room temperature. The suspension is cooled to 0-4° C., then it is hydrogenated at 2 bars of hydrogen gas without exceeding 8° C. The conversion is monitored using HPLC and it is deemed complete when the HPLC area % of the initial product and the reaction intermediates is <0.3. Then catalyst is filtered and the solution can be used as it is in the subsequent step or concentrated under vacuum at 45-50° C. to oily residue. About 86 g of yellow to dark red oil are obtained (about 98% yield, ee≥97%, purity ≥92%).

Preparation of the (2S,3R)-3-(3-Amino-phenyl)-1-(dimethylamino)-2-methyl-pentan-3-ol (XIV)

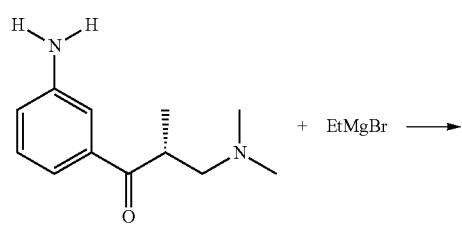

(XII)
MW = 206.29
MF = C12H18N2O
(S) 1-(3-amino-phenyl)-3-dimethylamino-2-methy-propan-1-one

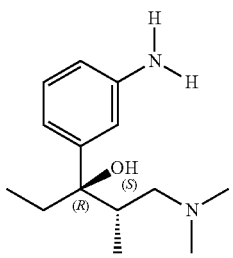

(XIV)
MW = 236.36
MF = C14H24N2O
(2S,3R)-3-(3-amino-phenyl)-1-dimethylamino-2-methyl-pentan-3-ol 726 ml of ethylmagnesium bromide (1M in THF; 0.726 mol) are added under a nitrogen flow into a 2-liter four-neck flask, provided with mechanical stirrer, thermometer and dropping funnel. A solution of (S)-3-(dimethylamino)-2-methyl-1-(3-nitro-phenyl)-propan-1-one (50 g, 0.242 mol) in 50 ml of THF are dripped maintaining the temperature between 15-30° C. The reaction is stirred at room temperature for 3 hours. It is cooled to about 10° C. and toluene (200 ml) and slowly a 20% ammonium hydrogen sulphate solution (200 ml) are added. The mixture is stirred for 30 minutes and the phases are separated after about 15 minutes of rest. The organic phase is concentrated under vacuum almost to oily residue. Then toluene (200 ml), 30% sodium metabisulfite solution (300 ml) are added. The mixture is stirred for 30 minutes and the phases are separated after about 15 minutes of rest. The aqueous phase is washed 2 times with 200 ml of toluene. The organic phases are eliminated while tert-butyl-methylether (200 ml) is added to the aqueous phase. The pH of the mixture is brought to 11-12 with 28% sodium hydroxide. The mixture is stirred for 30 minutes and the phases are separated after about 15 minutes of rest. The aqueous phase is eliminated while the organic phase is concentrated under vacuum to oily residue which solidifies by cooling. 35 g of a yellowish solid with a 95% HPLC purity are obtained.

Preparation of the (2R,3R)-dimethyl-[2-methyl-3-(3-nitro-phenyl)-pentyl]-amine (X)

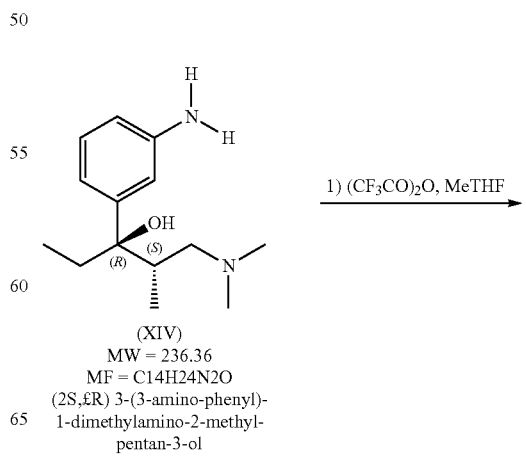

(XIV)
MW = 236.36
MF = C14H24N2O
(2S,£R) 3-(3-amino-phenyl)-1-dimethylamino-2-methyl-pentan-3-ol -continued

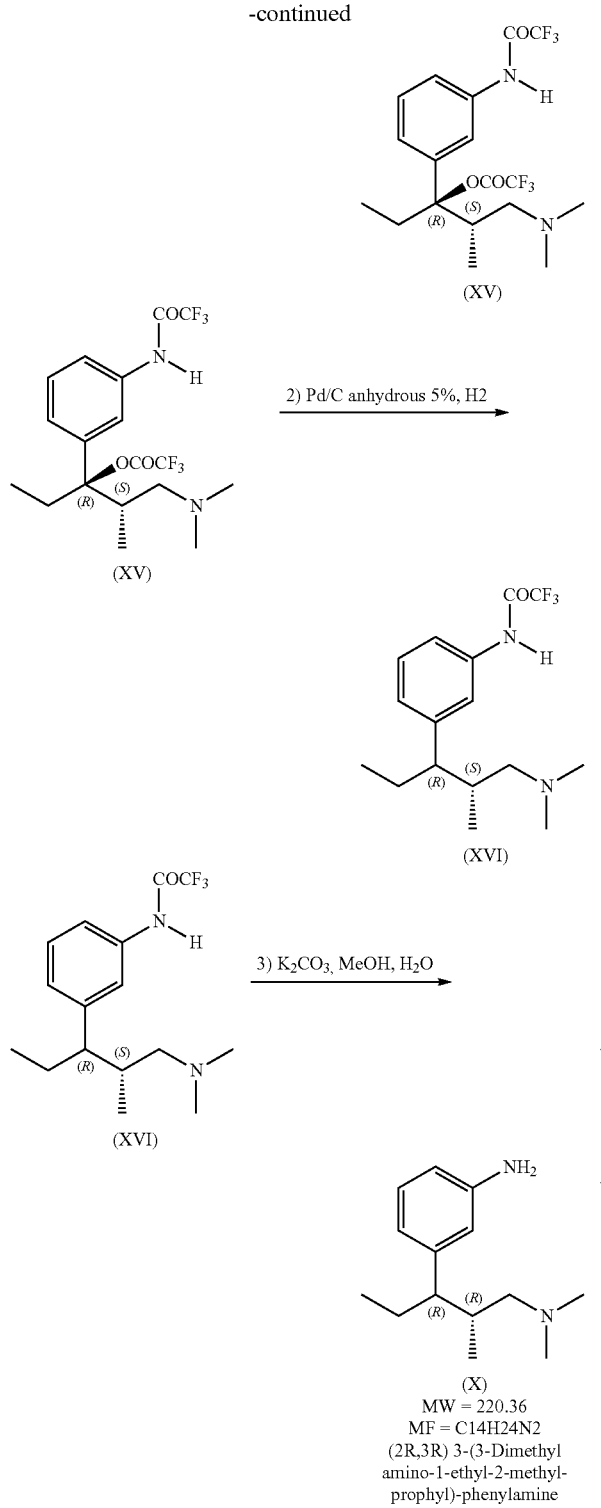

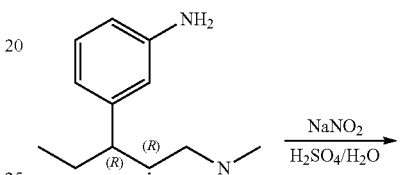

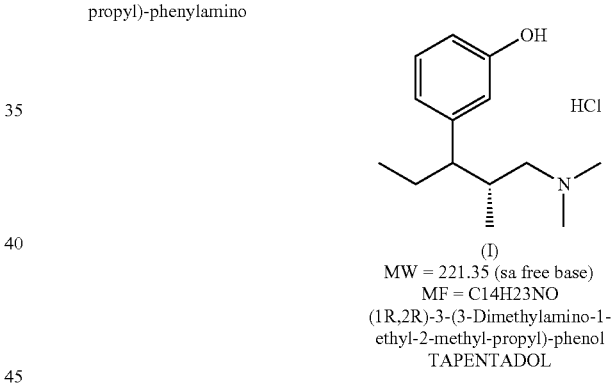

(2S,3R)-1-(dimethylamino)-3-(3-amino-phenyl)-2-methyl-3-pentanol (15 g, 0.0635 mol), Me-THF (60 ml) are added into a 250 ml four-neck flask, provided with mechanical stirrer, thermometer and dropping funnel and trifluoroacetic anhydride (30.7 g, 0.146 mol) is dripped maintaining the temperature <40° C. The mixture is stirred for 2-3 hours at 40° C. then conversion is monitored using HPLC. Upon completing esterification the reaction mixture is transferred into an autoclave, anhydrous Pd/C (0.75 g) is introduced. Hydrogenation is carried out at 6 bars with a temperature of 35-40° C. for 16-24 hours. When the reaction is complete the catalyst is filtered and the solution is concentrated under vacuum. 10% Potassium carbonate water/methanol (1:1, v/v) (200 ml) are added to the residue. The mixture is stirred for 12-24 hours at 35° C. then conversion is monitored using HPLC. The mixture is concentrated under vacuum at 40° C. to almost half the volume. Then toluene or TBME (100 ml) are added. The mixture is stirred for 30 minutes and the phases are separated after about 15 minutes of rest. The organic phase is concentrated under vacuum to obtain 12.6 g of oily residue with 98% HPLC purity.

Preparation of (1R,2R)-3-(3-dimethylamino-1-ethyl-2-methylpropyl)-phenol hydrochloride (I)

50 ml of 30-35% sulphuric acid are added into a 250 ml four-neck flask, provided with mechanical stirrer, thermometer and dropping funnel and cooled to 4° C. (2R,3R)-dimethylamino-1-ethyl-2-methyl-propyl)-phenylamine (10 g, 0.045 mol) is added to the cooled solution. A solution of $NaNO_2$ (3.4 g, 0.05 mol) dissolved in 10 ml of water is dripped into the cooled mixture. The reaction is stirred for 1 hour at 4° C. Then conversion is monitored using HPLC. 50 ml of 10-15% p/p sulphuric acid are added into another 250 ml four-neck flask provided with mechanical stirrer, thermometer, dropping funnel and condenser and brought to about 110° C. The cold solution of the diazonium salt is slowly dripped into the diluted sulphuric acid solution so as to control the formation of foam. The solution, after complete pouring, is maintained at 90-100° C. for about 15 minutes then it is cooled to 10-15° C. and the pH is brought to 10-11 with 28% sodium hydroxide. The product is extracted with ethyl acetate (100 ml). The organic phase is concentrated under vacuum at 40-50° C. to oily residue. The oil is dissolved in 3-pentanone (100 ml) and the hydrochloric acid gas (2.0 g, 0.05 mol) is absorbed under stirring at 20-25° C. A suspension that is left under stirring for 24 hours at room temperature is obtained. The solid is then filtered, washed with acetone and subsequently recrystallised from isopropanol. 10 g of white solid with HPLC purity >99% are obtained.

The invention claimed is:

1. A process for the synthesis of tapentadol comprising the following steps:

a) reaction of a racemic mixture of compound (V)

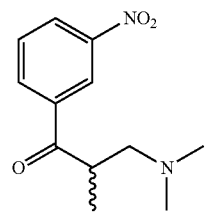
(V)

with a chiral acid in a polar solvent or mixture of polar solvents and subsequent precipitation of chiral salt (VI)

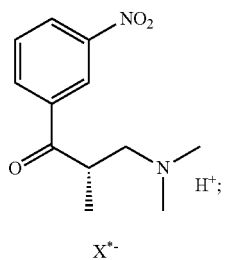
(VI)

b) treatment of the chiral salt (VI) with an aqueous base solution to obtain compound (VII)

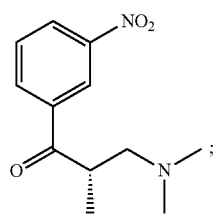
(VII)

c) extraction with an organic solvent;

d) reduction of the nitro group of the compound of formula (VII) to an amino group, to obtain a compound of formula (XII):

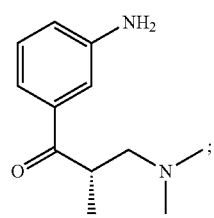
(XII)

e) conversion of the compound of formula (XII) into a compound of formula (XIV) by reaction with an organometallic reagent

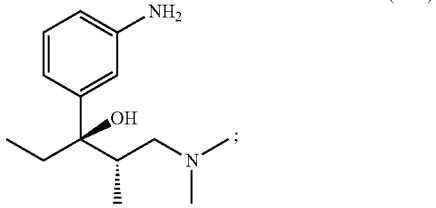
(XIV)

f) reaction of the compound (XIV) with an anhydride or a halide of an organic acid followed by hydrogenation to obtain, after hydrolysis, the compound of formula (X):

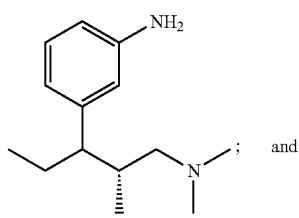
(X)

and g) the compound (X) is subjected to a diazotation reaction to obtain a diazonium salt of formula (XI):

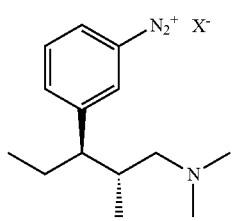
(XI)

which is subjected to hydrolysis conditions to obtain tapentadol, wherein X is the anion resulting from the diazotation reaction that is carried out in an aqueous solution of a mineral acid selected from sulfuric acid, hydrochloric acid, phosphoric acid, methansulfonic acid, and trifluoroacetic acid, and wherein X*— is the anion resulting from the reaction with the chiral acid in step a) selected from D(−)mandelic acid, D(−)2-chloro mandelic acid, D(−)tartaric acid, and (2R,3R)—O,O'-dibenzoyl tartaric acid.

2. The process according to claim 1, wherein the chiral acid is (2R,3R)—O,O'-dibenzoyl tartaric acid.

3. The process according to claim 1, wherein the polar solvent used in step a) is selected from water, aliphatic ketones, aliphatic alcohols and mixtures thereof.

4. The process according to claim 3, wherein the aliphatic ketone is acetone and the aliphatic alcohol is selected from methanol, ethanol, 1-propanol, 2-propanol and mixtures thereof.

5. The process according to claim 3, wherein the polar solvent is a methanol and acetone mixture.

6. The process according to claim 1, wherein the aqueous base solution used in step b) is an aqueous base solution of an alkali metal or alkaline earth metal hydroxide.

7. The process according to claim 6, wherein the aqueous base solution is an aqueous base solution of sodium hydroxide or potassium hydroxide.

8. The process according to claim 1, wherein the organic solvent used in step c) is toluene, tert-butyl methyl ether or iso-butyl ketone.

9. The process according to claim 8, wherein the organic solvent is tert-butyl methyl ether.

10. The process according to claim 1, wherein the reduction in step d) is carried out using tin and hydrochloric, acid.

11. The process according to claim 10, wherein the reduction is carried out in an aliphatic alcohol.

12. The process according to claim 11, wherein the reduction is carried out in ethanol.

13. The process according to claim 1, wherein the reduction in step d) is carried out using hydrogen and a catalyst.

14. The process according to claim 13, wherein the reduction is carried out in tetrahydrofuran, methyltetrahydrofuran, and/or toluene.

15. The process according to claim 13, wherein the reduction is performed at a temperature between −10 and 100° C.

16. The process according to claim 15, wherein the reduction is performed at a temperature between 0 and 15° C.

17. The process according to claim 1, wherein the organometallic reagent employed in step e) is derived from an ethyl halide and a metal.

18. The process according to claim 17, wherein the ethyl halide is ethyl bromide and the metal is zinc or magnesium and/or the process is carried out at a temperature between 10 and 30° C. and/or the organometallic reagent is used in a molar ratio of 1 to 5 equivalents with respect to compound (XII).

19. The process according to claim 1, wherein the anhydride or the halide of the organic acid employed in step f) is an anhydride or a halide of an aliphatic or aromatic organic acid, which may be optionally substituted.

20. The process according to claim 19, wherein the anhydride or the halide of the organic acid is selected from a $C_1$-$C_5$ alkyl acid, optionally substituted by 1-3 halogen atoms; a benzoic acid optionally substituted with 1-3 halogen atoms, alkyl and/or carboxyl groups; a phenylacetic acid, optionally substituted with 1-3 halogen atoms, alkyl and/or carboxyl groups; and a $C_1$-$C_6$ dicarboxylic acid and $C_1$-$C_4$ aliphatic esters thereof.

21. The process according to claim 19, wherein the anhydride or halide of the organic acid is an anhydride or halide of acetic acid, phenylacetic acid, chloroacetic acid, trifluoroacetic acid, benzoic acid, chloro benzoic acid, phthalic acid, succinic acid, oxalic acid or $C_1$-$C_4$ monoesters of oxalic acid or mixed anhydride of formic acid.

22. The process according to claim 21, wherein the anhydride or halide of the organic acid is an anhydride or halide of trifluoroacetic acid.

23. The process according to claim 1, wherein the anhydride of an organic acid employed in step f) is used in a molar ratio of 1 to 5 equivalents with respect to compound (XIV).

24. The process according to claim 1, wherein the hydrogenation in step f) is carried out in the presence of palladium on charcoal.

25. The process according to claim 24, wherein the hydrogenation is carried out at a pressure between 1 and 100 bar and/or a temperature between 0 and 100° C.

26. The process according to claim 1, wherein the diazotation reaction is carried out in an aqueous solution of sulfuric acid in the presence of sodium nitrite.

27. The process according to claim 1, wherein the diazotation reaction is carried out at a temperature between −15 and 50° C.

* * * * *

UNITED STATES PATENT AND TRADEMARK OFFICE
CERTIFICATE OF CORRECTION

Page 1 of 1

PATENT NO. : 8,729,308 B2
APPLICATION NO. : 13/512989
DATED : May 20, 2014
INVENTOR(S) : Giuseppe Motta, Domenico Vergani and Giorgio Bertolini It is certified that error appears in the above-identified patent and that said Letters Patent is hereby corrected as shown below:

Title Page, item [73] Assignee Address: "Milan" should be --Milano--.

Title Page, Foreign Patent Doc: "EP0593475" should be --EP0693475--.

Title Page, Foreign Patent Doc: "WO2006/012283" should be --WO2008/012283--.

Signed and Sealed this
Twelfth Day of August, 2014

Michelle K. Lee
*Deputy Director of the United States Patent and Trademark Office*